United States Patent
Mertz

(10) Patent No.: US 10,641,739 B2
(45) Date of Patent: May 5, 2020

(54) METHOD AND SYSTEM FOR OBLIQUE BACKSCATTERING ULTRASOUND TRANSMISSIVE CONTRAST IMAGING

(71) Applicant: TRUSTEES OF BOSTON UNIVERSITY, Boston, MA (US)

(72) Inventor: Jerome Charles Mertz, Newton, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 15/538,802

(22) PCT Filed: Dec. 23, 2015

(86) PCT No.: PCT/US2015/000245
§ 371 (c)(1),
(2) Date: Jun. 22, 2017

(87) PCT Pub. No.: WO2016/105509
PCT Pub. Date: Jun. 30, 2016

(65) Prior Publication Data
US 2017/0363582 A1    Dec. 21, 2017

Related U.S. Application Data

(60) Provisional application No. 62/095,996, filed on Dec. 23, 2014.

(51) Int. Cl.
*G01N 29/06* (2006.01)
*A61B 8/00* (2006.01)
(Continued)

(52) U.S. Cl.
CPC .......... *G01N 29/0681* (2013.01); *A61B 8/15* (2013.01); *A61B 8/4494* (2013.01); *A61B 8/48* (2013.01);
(Continued)

(58) Field of Classification Search
None
See application file for complete search history.

(56) References Cited

U.S. PATENT DOCUMENTS

| 3,711,823 A | * | 1/1973 | Green | G01H 9/002 |
| | | | | 181/402 |
| 4,803,994 A | | 2/1989 | Burke | |

(Continued)

FOREIGN PATENT DOCUMENTS

| CN | 10298009 A | 9/2011 |
| WO | 2013148360 A1 | 3/2013 |

OTHER PUBLICATIONS

Chu et al. "Graded-field autoconfocal microscopy," Opt. Express, vol. 15, No. 5, pp. 2476-2489, 2007.
(Continued)

*Primary Examiner* — Tahmina N Ansari
(74) *Attorney, Agent, or Firm* — Nixon Peabody LLP; Ronald I. Eisenstein; David F. Crosby

(57) ABSTRACT

An Oblique Backscatter Ultrasound imaging system includes a transceiver that has an US source and a plurality of US detectors configured in receive signals off axis from the US source. While the system is arranged in a reflective configuration, the device produces transmissive contrast signals to yield improved images. The transceiver can be mounted to a movable stage or robotic arm to enable it to scan the surface of a target. Alternatively, scanning can be performed by 1D or 2D phased-array transmission or detection.

14 Claims, 9 Drawing Sheets

(51) Int. Cl.
*A61B 8/15* (2006.01)
*G01S 7/52* (2006.01)
*A61B 8/08* (2006.01)
*G01S 15/89* (2006.01)

(52) U.S. Cl.
CPC ...... *G01S 7/52046* (2013.01); *G01S 7/52085* (2013.01); *G01S 15/8913* (2013.01); *A61B 8/4218* (2013.01); *A61B 8/4488* (2013.01); *A61B 8/5261* (2013.01); *A61B 8/54* (2013.01); *G01N 2291/044* (2013.01)

(56) References Cited

U.S. PATENT DOCUMENTS

| 4,829,430 | A | 5/1989 | Greenleaf et al. | |
|---|---|---|---|---|
| 5,433,202 | A * | 7/1995 | Mitchell | A61B 8/0825 128/915 |
| 6,200,268 | B1 | 3/2001 | Vince et al. | |
| 6,238,346 | B1 | 5/2001 | Mason | |
| 6,277,074 | B1 * | 8/2001 | Chaturvedi | A61B 8/0833 600/437 |
| 7,757,558 | B2 | 7/2010 | Bossi et al. | |
| 7,999,945 | B2 | 8/2011 | Zara | |
| 2004/0258759 | A1 * | 12/2004 | Suslick | A61K 49/001 424/490 |
| 2006/0184042 | A1 | 4/2006 | Wang et al. | |
| 2006/0184033 | A1 * | 8/2006 | Cerofolini | A61B 8/00 600/459 |
| 2013/0269441 | A1 | 10/2013 | Doyle et al. | |
| 2017/0363582 | A1 * | 12/2017 | Mertz | G01N 29/0681 |

OTHER PUBLICATIONS

Allen et al. "The Zeiss-Nomarski differential interference equipment for transmitted light microscopy," Z. Wiss. Mikrosk., vol. 69, pp. 193-221, 1969.

Ford et al. "Video-rate imaging of microcirculation with single-exposure oblique back-illumination microscopy single-exposure oblique back-illumination microscopy." Journal of biomedical optics 18(6) (2013):066007.

Ford et al., "Fast volumetric phase-gradient imaging in thick samples," 22(1): 21843-21848 (2014).

Johnston et al. "Acoustic microscopy: resolution of subcellular detail.," Proc. Natl. Acad. Sci. U. S. A., vol. 76, No. 7, pp. 3325-9, Jul. 1979.

Mertz "Phase-gradient contrast in thick tissue with a scanning microscope.," Biomed. Opt. Express, vol. 5, No. 2, pp. 407-16, Feb. 2014.

Yi et al. "Graded-field microscopy with white light," Opt. Express, vol. 14, pp. 5191-5200, 2006.

Mehta et al. "Quantitative phase-gradient imaging at high resolution with asymmetric il+A24:A27lumination-based differential phase contrast.," Opt. Lett., vol. 34, No. 13, pp. 1924-6, Jul. 2009.

Ford et al. "Phase-gradient microscopy in thick tissue with oblique back-illumination", Nat. Methods, 9(12): 1195-1197 (2012).

Zernike "How I discovered phase contrast." Science 121(3141): 345-349 (1955).

Hildebrand et al. "Acoustic microscopy of living cells.," Proc. Natl. Acad. Sci. U. S. A., vol. 78, No. 3, pp. 1656-60, Mar. 1981.

Sheppard et al. "On the equivalence of scanning and conventional microscopes," Optik (Stuttg)., vol. 73, pp. 39-43, 1986.

Bude et al. "An Easily Made, Low-Cost, Tissue-Like Ultrasound Phantom Material," J. Clin. Ultrasound, vol. 23, pp. 271-273, 1995.

Dodt et al. "Precisely localized LTD in the neocortex revealed by infrared-guided laser stimulation," Science (80-. ).,vol. 286, No. 5437, p. 110, 1999.

Dubois et al. "High-resolution full-field optical coherence tomography with a Linnik microscope," Appl. Opt., vol. 41, pp. 805-812, 2002.

Wolff, B. et al., "EN Face OCT Imaging for the Diagnosis of Outer Retinal Tubulations in Age-Related Macular Degeneration", Clinical Journal of Ophthalmology (2012) Article 542417.

Barnett "The reciprocity theorem and the equivalence of conventional and transmission microscopes," Optik (Stuttg)., vol. 38, pp. 585-588, 1973.

Burlew et al. "A new ultrasound tissue-equivalent material," Radiology, vol. 134, p. 517, 1980.

Dodd "Interferometry with Schlieren microscopy," Appl. Opt., vol. 16, pp. 470-472, 1977.

Fujimoto "Optical coherence tomography for ultrahigh resolution in vivo imaging," Nat. Biotechnol., vol. 21, No. 11, pp. 1361-1367, 2003.

Hoffman et al. "Modulation contrast microscopy," Appl. Opt., vol. 14, pp. 1169-1176, 1975.

Kermisch "Principle of equivalence between scanning and conventional optical imaging systems," J. Opt. Soc. Am, vol. 67, No. 1357-1360, 1977.

Nomarski "Microinterferometre differentuiel a ondes polarisees," J. Phys. Radium, . 16:S9 (1955).

Welford "On the relationship between the modes of image formation in scanning microscopy and conventional microscopy," J. Microsc., vol. 96, pp. 104-107, 1972.

* cited by examiner

*(OBM Images)*

*(OCT Images)*

Reflection mode

Transmission mode

METHOD AND SYSTEM FOR OBLIQUE BACKSCATTERING ULTRASOUND TRANSMISSIVE CONTRAST IMAGING

CROSS-REFERENCE TO RELATED APPLICATIONS

This application is a 35 U.S.C. § 371 National Phase Entry Application of International Application No. PCT/US2015/000245 filed on Dec. 23, 2015, which designates the U.S., and which claims any and all benefits as provided by law including benefit under 35 U.S.C. § 119(e) of the U.S. Provisional Application No. 62/095,996, filed Dec. 23, 2014, the contents of each of which are incorporated herein by reference in its entirety their entireties.

STATEMENT REGARDING FEDERALLY SPONSORED RESEARCH

This invention was made with Government support under Contract No. CA182939 awarded by the National Institutes of Health. The Government may have certain rights in this invention.

REFERENCE TO MICROFICHE APPENDIX

Not Applicable

BACKGROUND

Technical Field of the Invention

The present invention relates to ultrasound imaging and more specifically, to a modality referred to as Oblique Backscattering UltraSound (OBUS) imaging that is based on the detection of transmitted sound through an object or tissue. OBUS imaging can be used to reveal fundamentally different target features than traditional ultrasound and provide speckle-free images.

Description of the Prior Art

Ultrasound (US) imaging is a common method of medical imaging, and has had a significant impact in the practice and delivery of healthcare. Advantages of ultrasound imaging are that it is non-invasive, cost-effective, and provides images with penetration depths commensurate with human organ imaging. In this last regard, US imaging has a considerable advantage over optical imaging techniques, which are hampered by very poor depth penetration in comparison.

Historically, phase contrast imaging is one of the most prevalent applications of wide-field optical microscopy, and there exists an abundance of literature describing different wide-field phase contrast techniques. The most common of these, found in virtually every cellular biology lab, are Zernike phase contrast [7] and Normarski differential interference contrast (DIC) [8], [9] imaging systems. The latter is also widely used in neurophysiology labs, since it is highly effective at revealing neurons in brain tissue slices. Other wide-field phase contrast techniques include Schlieren microscopy [10], Hoffman contrast [11], Dodt contrast [12] or other variants of oblique field microscopies such as our own graded field contrast [13], [14]. As successful as these techniques have been in the lab, they suffer a major drawback: namely they work only in the transmission direction. This limits these techniques to thin samples only, such as cell monolayers or thin tissue slices.

A new optical microscopy technique called Oblique Back-illumination Microscopy (OBM) can be used to provide DIC-like phase contrast images in arbitrary thick tissue. And while OBM is a remarkably simple method to obtain fast, high resolution, label-free imaging of tissue structure, it is limited in depth penetration to about 100 μm. Such limited depth penetration restricts the applicability of OBM to superficial imaging of epithelial tissue only.

Standard epi-detection wide-field microscopy is based on delivering illumination into the sample or target through an objective and collecting the resultant signal (fluorescence or otherwise) through the same objective. One difference between OBM and a standard epi-detection wide-field microscope is in the manner the illumination is delivered to the sample or target. Instead of delivering this illumination through the objective, in the OBM system, it is delivered by two off-axis light sources just outside the objective housing and distributed diametrically opposite each other as shown in FIG. 1A. This illumination undergoes scattering within the tissue, and only a portion of this illumination is collected on axis by the objective to be ultimately imaged by the camera. As it happens, because the light sources are off axis this collected illumination traverses the focal plane of interest in an oblique manner, thus leading to phase gradient contrast [15], [16]. The advantage of using two light sources instead of a single source is that it allows the acquisition of two sequential images with opposite illumination obliquity. These two images enable the separation of phase contrast (FIG. 1B bottom) from amplitude contrast (FIG. 1B top) [3].

OBM is not the only optical imaging modality that can provide phase contrast in arbitrarily thick tissue. Optical Coherence Tomography (OCT) also reveals index of refraction (and hence phase) variations within samples (or targets) [17], and because it is arranged in a reflection configuration, it too can provide imaging in arbitrarily thick samples or targets. FIGS. 2A and 2B provide a comparison of OCT (FIG. 2A) and OBM (FIG. 2B) images of the same sample with both instruments. The sample in this case was excised mouse skin. The figures show the differences between OCT and OBM images. They are all the more striking when one considers that both modalities reveal the same thing, namely index of refraction variations. The reason for these differences comes from the fact that OCT is a reflection microscope, whereas OBM is fundamentally a transmission microscope (even though it is configured in a reflection direction). This difference is highlighted in FIGS. 3A and 3B. While a reflection contrast is based on very strong axial momentum transfers imparted to light (strong enough to cause light to reverse its direction), transmission contrast is based instead on much weaker lateral momentum transfers. That is, a reflection microscope inherently reveals only sample structure that contains strong axial variations (i.e. rapidly varying axial spatial frequencies), while a transmission microscope reveals much weaker lateral sample structure (i.e. slowly varying lateral spatial frequencies). These theoretical expectations are demonstrated in FIGS. 2A and 2B, where we observe that OCT reveals only small objects or sharp interfaces, while OBM reveals objects that are slowly varying. In principle, the complementary information provided by both modalities could be combined to provide a much more complete picture of the imaged objects.

FIGS. 2A and 2B reveal another apparent difference between OCT and OBM, specifically OCT images appear highly degraded by speckle noise, whereas OBM images are manifestly speckle-free. The reason for this is that OCT is a coherent imaging method based on the interference between target and reference beams, while OBM is a purely intensity based technique that does not rely on interference. Because OBM is intensity based, it can be operated with light sources as simple as LEDs.

SUMMARY

Conventional Ultrasound (US) imaging is a common and well known method of medical imaging that uses reflected audio waves to produce images of features below the surface of a person, an animal or an object. Its range of applications is enormous, spanning anesthesiology, cardiology, emergency medicine, gastroenterology, gynecology, otolaryngology, neonatology, neurology, obstetrics, ophthalmology, pulmonology, urology, and more fields. The advantages of ultrasound imaging are that it is non-invasive, cost-effective, and provides images with penetration depths commensurate with human organ imaging. In this last regard, US imaging has a considerable advantage over optical imaging, which is hampered by very poor depth penetration in comparison.

Oblique Backscattering UltraSound (OBUS) imaging according to the invention can utilize audio waves to produce images of features below the surface. In accordance with some embodiments, OBUS can be based on the detection of transmitted rather than reflected sound (even though it can be configured in a reflection geometry). Such imaging can be used to reveal fundamentally different sample or target features. Moreover, such imaging will be speckle-free, which has been a long-standing challenge in US imaging.

In accordance with some embodiments, one difference between OBUS and standard US imaging is that OBUS can be used to reveal fundamentally different target structures because it is based on transmission rather than reflection (even though OBUS imaging is configured in a reflection geometry). As a result, according to some embodiments, OBUS can use a fundamentally different strategy for acoustic imaging that can reveal subtler tissue density variations than standard US and can reveal sample or target structure previously inaccessible. Moreover, OBUS images can be speckle-free, which has been a longstanding challenge in the US imaging.

In accordance with some embodiments of the invention, the OBUS imaging system can include one or more receiving audio transducers or sensors and two more transmitting audio transducers arranged around (e.g., flanking) the receiving transducer. The transmitting audio transducers can produce one or more audio signals or waves (e.g., ultrasound) that penetrate into the target, become disbursed within the target material and then are subsequently received by the receiving audio transducer. The receiving audio transducer receives at least a portion of the audio signals or waves. Each transmitting audio transducer can focus the audio signals or waves on a focal spot or plane within the target. The receiving transducer and the transmitting transducers can be configured to move over or scan an area of the target to generate an image of the object along the focal plane. The image can be constructed by combining the audio signals received or sensed as the OBUS imaging system is scanned over the surface of the target.

In accordance with some embodiments of the invention, an array of receiving audio transducers or sensors can be configured to individually sense audio signals passing through a target. The array of receiving audio transducers can be, for example, one dimensional or two dimensional. Where the array is one dimensional (e.g., in the X dimension), the OBUS system can be scanned in the other dimension (e.g., the Y dimension) to produce an image of the scanned area. Where the array is two dimensional, the scanning can be achieved electronically, by individually or selectively accessing the audio receiving transducers to cover a predefined area according to the receiving audio transducers selected.

In accordance with some embodiments of the invention, the target can be an animal, a person or a thing that permits audio signals or waves can pass through. Typically, the target can be human or animal tissue, such as for imaging into the body below the surface of the skin. In other embodiments, the target can be a tissue sample excised from a source (e.g., a biopsy). In other embodiments, the target could be an object or part of object, such as a wall or surface (e.g., for detecting subsurface defects in materials and pipe).

In accordance with some embodiments of the invention, the OBUS imaging system can include one or more transmitting audio transducers and two more receiving audio transducers or sensors arranged around (e.g., flanking) the transmitting transducer. The transmitting audio transducer can produce one or more audio signals or waves (e.g., ultrasound) that penetrate into the target, become disbursed within the target material and then are subsequently received by each of the receiving audio transducers or sensors. Each of the receiving audio transducers or sensors receives at least a portion of the audio signals or waves. Each transmitting audio transducer can focus the audio signals or waves on a focal spot or plane within the target. The receiving audio transducers and the transmitting transducer can be configured to move or scan an area of the target to generate an image of the object along the focal plane. The image can be constructed by combining the audio signals received or sensed as the OBUS imaging system is scanned over the surface of the target.

In accordance with some embodiments, the audio transmitting transducer can be configured as a point source that can be mounted to a robotic arm or an X-Y gantry or stage that can move the audio transmitting transducer in the X and Y dimensions to scan an area. In accordance with some embodiments of the invention, an array of transmitting audio transducers or sensors can be configured to individually produce audio signals that penetrate the target. The audio transmitting transducers can be configured in a one dimensional array or a two dimensional array. Where the array is one dimensional (e.g., in the X dimension), the OBUS system can be scanned (e.g., moved or translated) in the other dimension (e.g., the Y dimension) to produce an image of the scanned area. Where the array is two dimensional, the scanning can be achieved electronically, by individually or selectively operating the transmitting audio transducers to cover a predefined area according to the transmitting audio transducers selected.

In accordance with some embodiments of the invention, the OBUS system can be constructed from an array of US transceiving transducers that can be selectively operated as transmitters or receivers according to predefined configurations. In accordance with some embodiments, the OBUS system can include one or more pairs of audio transmitting and receiving pairs of transducers (e.g., right next to each other) that can be selectively operated.

In accordance with some embodiments, OBUS imaging can be fully compatible with standard US imaging. Specifically, OBUS and US imaging can be operated simultaneously and provide complementary images that can be automatically co-registered. This will facilitate the interpretation of OBUS images, which can be different from standard US images.

One of the objects of the invention is to perform imaging analogous to OCT and OBM, but in the acoustic domain.

There is a well-known analogy between optical imaging and US imaging that stems from the fact that both are based on the wave equation. The main difference between the two modalities lies in differences between their scales of space and time. While wavelengths and frequencies in optics are on the order of microns and hundreds of terahertz, respectively, in medical acoustics they are on the order of millimeters and megahertz. As a result, wave speeds in optics are on the order of $10^8$ m/s, whereas in medical acoustics they are on the order of $10^3$ m/s.

The analogy between optics and acoustics is even closer when one compares OCT to US imaging. Both are based on the identical principle of axial ranging based on temporal gating. In OCT, this temporal gating is achieved optically by interference with a temporally coherent reference beam. In US imaging, the time scales are slow enough that it can be achieved directly by electronic time-keeping. Because the principles of OCT and US imaging are the same, the constraints that bind them are also the same. Specifically, standard US imaging only reveals sharp interfaces or small target structures, and it is confounded by speckle noise. This latter problem of speckle noise has been an issue in medical US imaging since its inception.

Another objection object of the invention is to generate acoustic images that do not look like standard US or OCT images (FIG. 2A), but instead look like OBM images (FIG. 2B). Just as OCT and OBM images are clearly different, the OBUS imaging technique according to the invention produces images that are clearly different (in the acoustic domain).

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

FIG. 2A shows a montage of representative Optical Coherence Tomography (OCT) images and FIG. 2B shows a montage of representative OBM images. The field of view are the same (scale bar=10 micrometers).

FIG. 6A shows a focused phased-array detection having two transmitting transducers and one phased-array receiving transducer. FIG. 6B shows focused phased-array transmission having a phased-array transmitter and two flanking receivers.

In accordance with some of the embodiments of the invention, the transceiver unit that includes the transmitter (Tx) and receiver (Rx) can be mounted to a mechanism that facilitates the scanning in one, two or three dimensions to follow the surface of the target to be scanned. In accordance with some embodiments of the invention, the transceiver unit can be mounted to a moveable stage that controls the physical motion of the transceiver unit in the X, Y, and/or Z dimensions. In accordance with some embodiments of the invention, the transceiver unit can be mounted to a moveable gantry that controls the physical motion of the transceiver unit in the X, Y, and/or Z dimensions. In accordance with some embodiments of the invention, the transceiver unit can be mounted to a robotic arm that controls the physical motion of the transceiver unit in the X, Y, and/or Z dimensions. While the description provided herein discloses motion according to Cartesian coordinates (e.g., X, Y, and Z) the mechanism can also be configured to move the transceiver unit according to a polar coordinate system

DETAILED DESCRIPTION OF PREFERRED EMBODIMENTS

The present invention is directed to methods and systems for acoustic imaging based on diffuse backscattering. One example of the invention includes Oblique Backscattering Ultrasound (OBUS) that produces images based on the detection of transmitted rather than reflected acoustic signals such as ultrasound. This OBUS imaging system can be used to reveal different target features and provide speckle-free images.

Figure 1B:
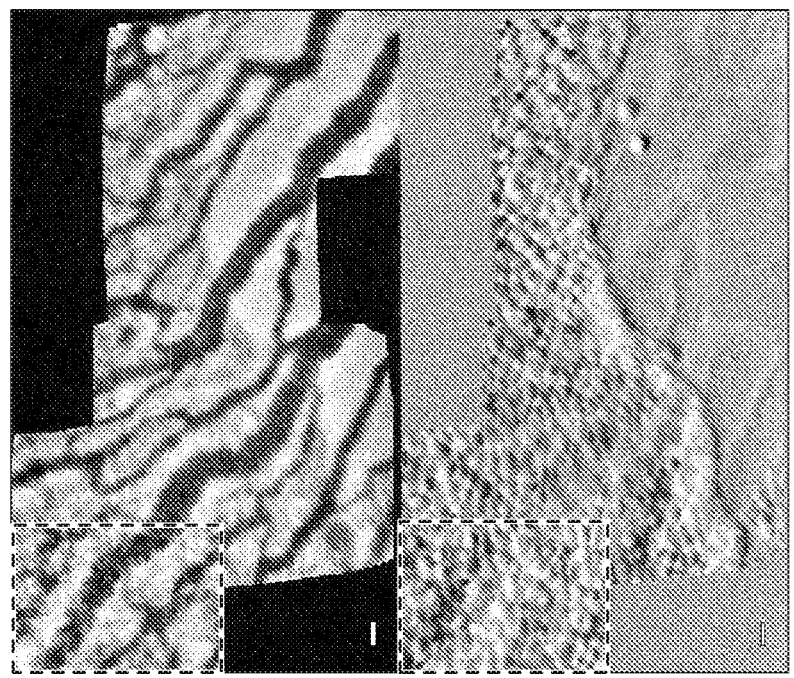
FIG. 1B shows the resulting images recorded by a camera are either added to produce amplitude contrast (top) or subtracted to produce phase-gradient contrast (bottom). The target here is a chick embryo in vivo (day 11). Amplitude contrast (top) reveals subsurface vasculature while phase gradient (bottom) reveals extravascular morphology. Mosaics are reconstructed from videos, illustrating possibility of extending the field of view to arbitrarily large sizes (single frames delimited by red dashed line). Scale bar 30 μm. See refs [3][4] for more details.
Figure 1A:
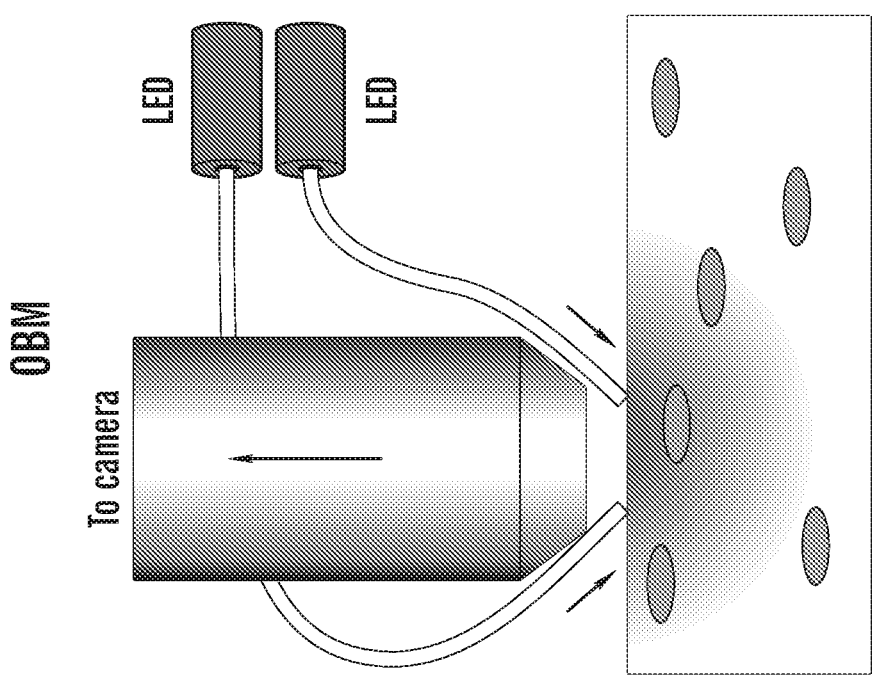
FIG. 1A shows a schematic of an Oblique Back-illumination Microscopy (OBM) system. A thick sample is illuminated sequentially by two LEDs via off-axis optical fibers.
Figure 2B:
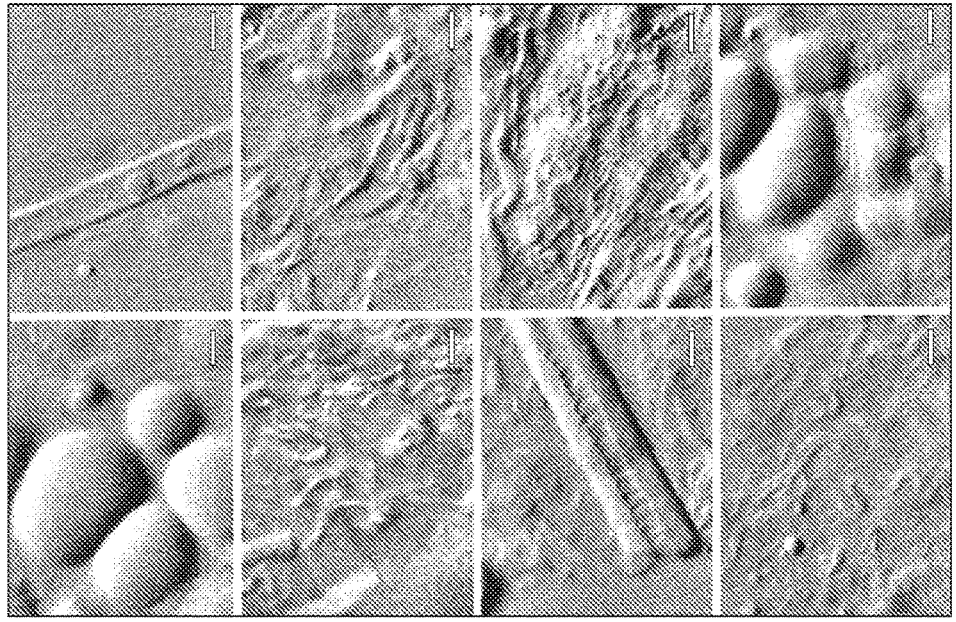
FIGS. 2A and 2B show a montage of representative images of excised mouse skin.
Figure 2A:
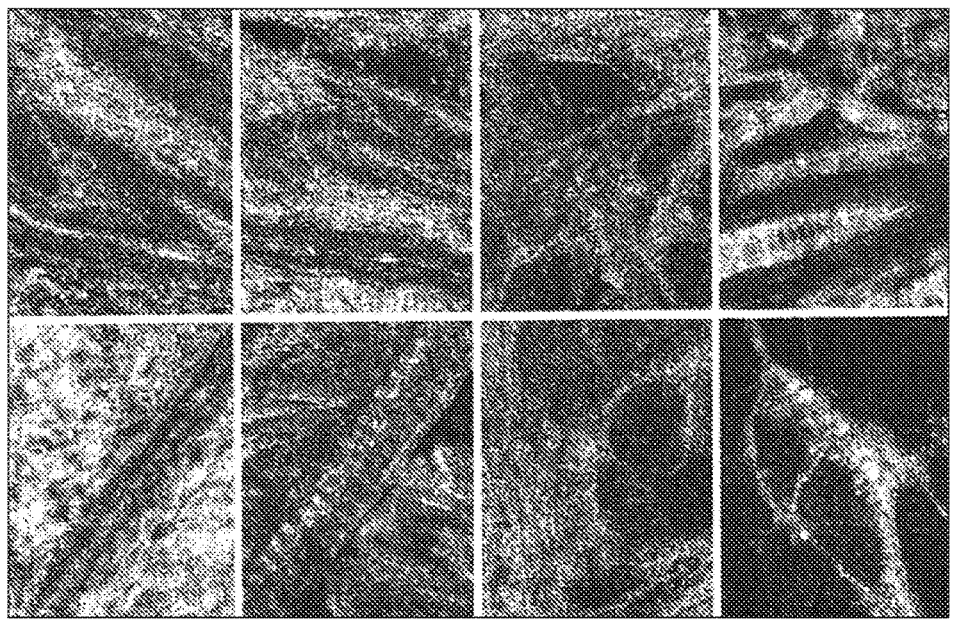
Figure 3A:
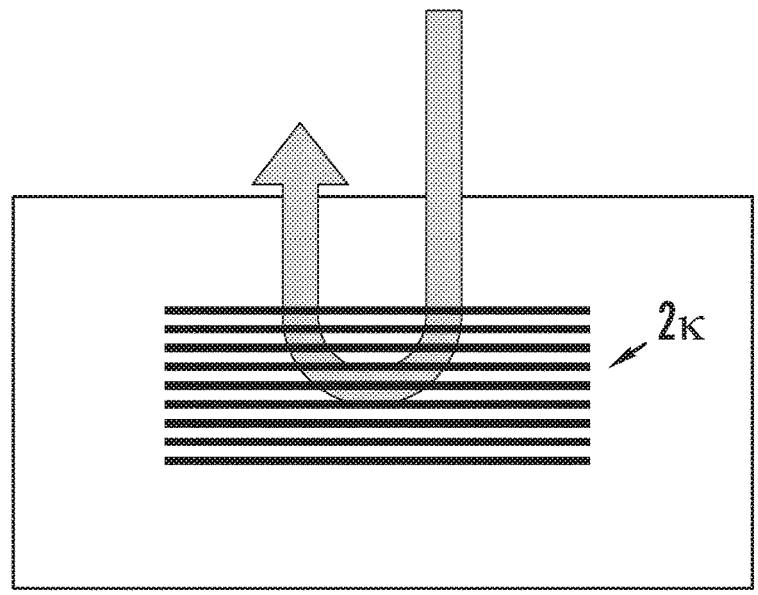
FIG. 3A shows a diagram of a reflection contrast imaging modality.
Figure 3B:
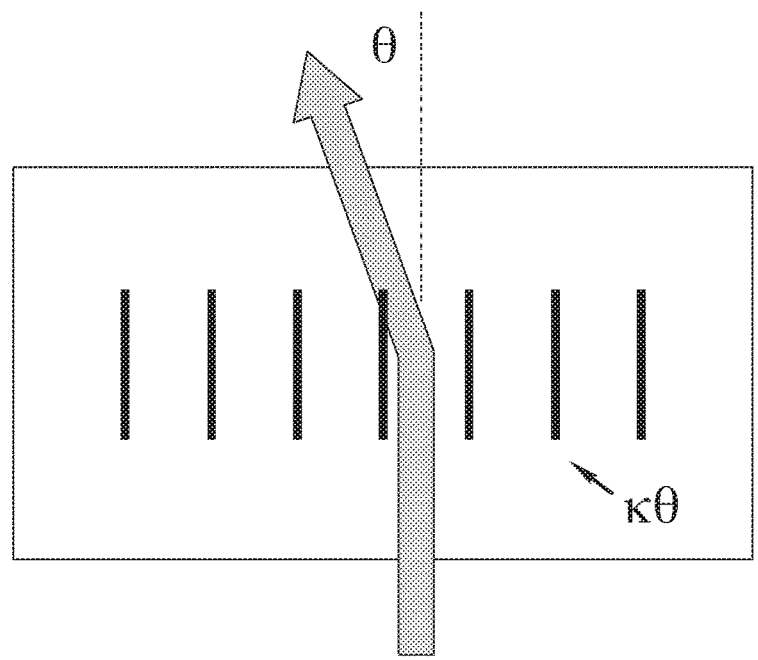
FIG. 3B shows a diagram of a transmission contrast imaging modality.

In constructing an OBUS system, one consideration is purely geometric—how to produce en-face (x-y) images. Standard medical Ultrasound (US) imaging provides cross-sectional (x-z) images, called B-scans [1]. It is possible to synthesize en-face images, called C-scans, but this requires the extra step of scanning the US probe in the orthogonal y direction to obtain volumetric data. FIG. 2A shows examples that are the optical equivalent of C-scans.

In accordance with some embodiments, the OBUS system can be constructed using various configurations of transmitting acoustic transducers (e.g. acoustic signal sources) and receiving acoustic transducers or sensors. In accordance with some embodiments of the invention, the US receiver can include a 2 dimensional array of acoustic (e.g. US) sensors or detectors and the transducers and/or the sensors can be configured to electronically scan an area by selectively operating one or more individual transducers or sensors. In accordance with some embodiments of the invention, the US receiver can include a 1 dimensional array of acoustic (e.g., US) sensors or detectors which can be scanned (e.g. moved or translated by a robot, stage or gantry) across a target to simulate a 2 dimensional array. In accordance with some embodiments of the invention, a single acoustic (e.g., US) sensor and/or detector which can be scanned (e.g. moved or translated by a robot, stage or gantry) in 2 dimensions to simulate a 2 dimensional array. In accordance with some embodiments of the invention, the acoustic transmitters and receivers can be mounted on a robotic arm, an X-Y gantry or stage to move the acoustic transmitters and receivers in one or more scanning patterns over an area.

In accordance with some embodiments of the invention, the transmitting US transducer (e.g., US source) can include a 2 dimensional array of acoustic (e.g. US) signal generators. In accordance with some embodiments of the invention, the transmitting US transducer can include a 1 dimensional array of acoustic (e.g., US) signal generators which can be scanned (e.g. moved or translated by a robot, stage or gantry) across a target to simulate a 2 dimensional array. In accordance with some embodiments of the invention, a single transmitting acoustic (e.g., US) transducer which can be scanned (e.g. moved or translated by a robot, stage or gantry) in 2 dimensions to simulate a 2 dimensional array.

Figure 4B:
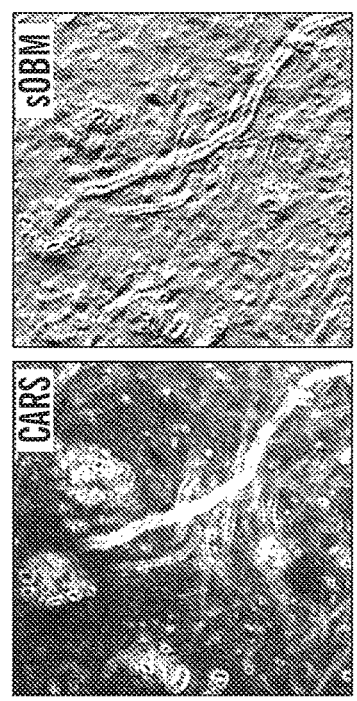
FIG. 4A shows a diagram of a scanning-OBM or sOBM system and FIG. 4B shows corresponding sOBM and CARS images.
Figure 4A:
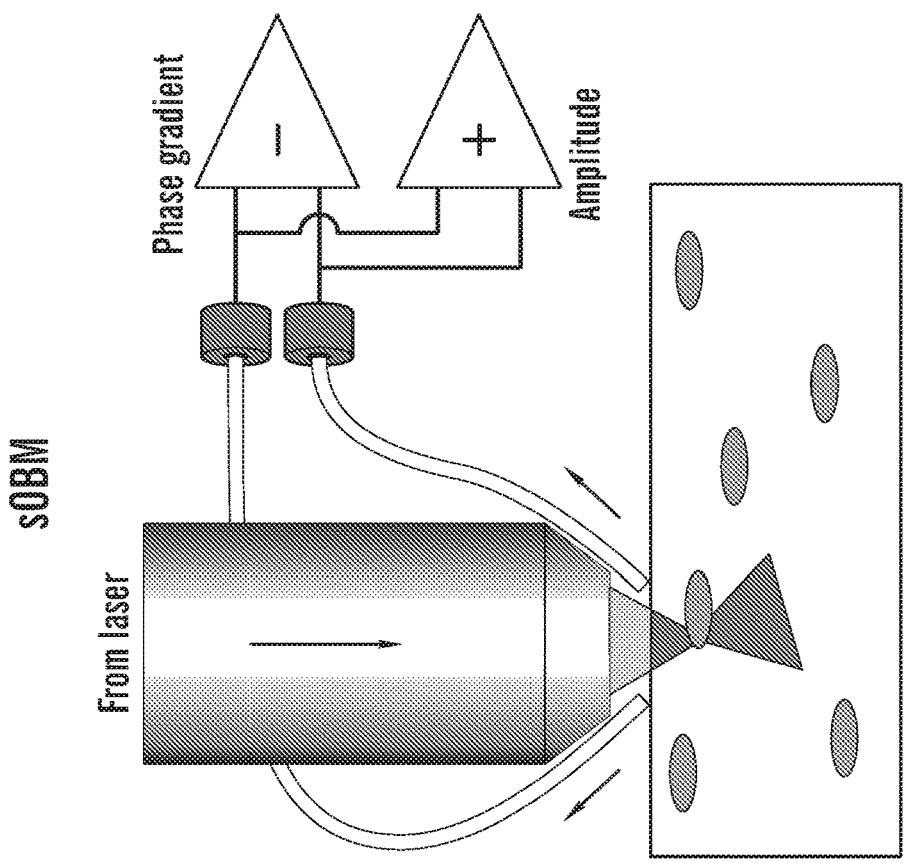

A scanning microscope is essentially a time-reversed version of a widefield microscope [19]-[22]. That is, if each pixel in the camera is replaced by an incoherent illumination source turned on sequentially, and the illumination lamp is replaced by a single element detector of equal size, the net result is a scanning microscope. Because of the principle of reciprocity [23], the imaging properties of widefield and scanning microscopes are identical, provided these are linear. This principle remains valid even if the target is highly scattering or exhibits absorption [24]. The scanning Oblique Back-illumination Microscopy (sOBM) is borne of this principle of reciprocity. sOBM is a time-reversed version of OBM wherein scanning illumination is delivered into the target via an on-axis objective and, upon back-scattering, is detected by two diametrically opposed off-axis detectors (see FIG. 4). A difference of the two detected signals provides phase gradient contrast; a sum provides amplitude contrast. In the case where the target presents little absorption, the difference signal is of most interest.

It can be useful that the OBUS deliver a focused beam into the target. This can be achieved in acoustics by using a single-element longitudinal-wave immersion US transducer (e.g. Panametrics, Olympus Corp., Waltham, Mass.) designed with a curved interface to provide a spherical (spot) focus. Such transducers can be designed to be partially or totally immersed, or can be operated with impedance-matching gels. The focus depth of such transducers can be a function of their design, and is typically in the range of several millimeters (e.g., 0.5-100 mm) to centimeters (e.g., 1-20 cm). The size of the focal spot can also depend on the design of the transducers (e.g., specifically their numerical aperture) and the acoustic wavelength of the signal. Based on rough calculations and manufacturer specifications, and for acoustic frequencies in the range 1-10 MHz, spot sizes on the order of 1 mm, or smaller can be generated. Generally, the spot size will inform the spatial resolution of our device.

Figure 5:
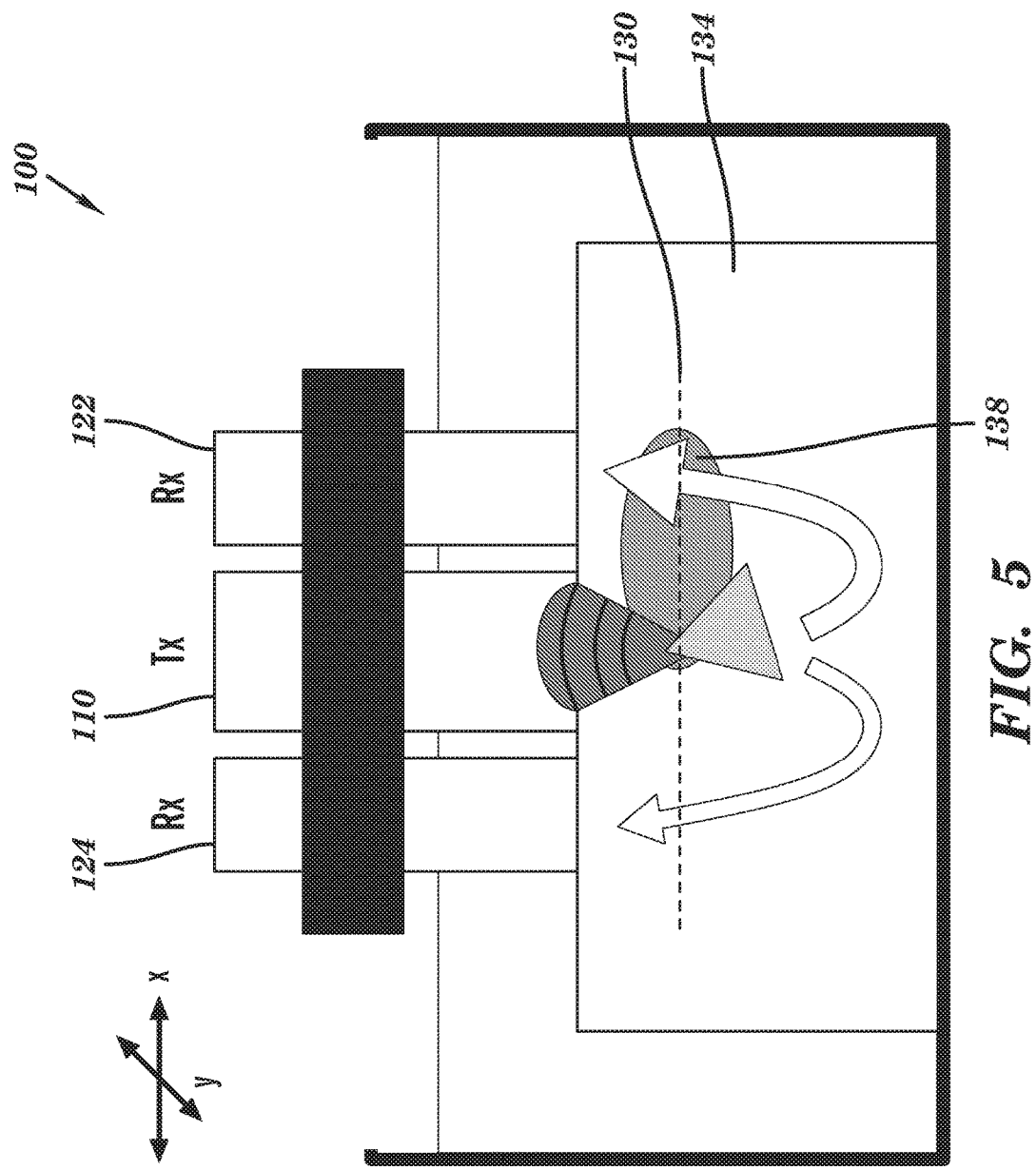
FIG. 5 shows a schematic diagram of an OBUS system according to the invention.

A schematic of an imaging system 100 according to some embodiments of the invention is shown in FIG. 5. In these embodiments, a central acoustic transmitting transducer 110 can be positioned between receiving detectors 122, 124. The acoustic transmitting transducer can be configured to produce a focal spot at a particular (e.g., predefined) depth which can be adjusted within the target 134 along the focal plane 130. The sound propagates through this focal plane 130 and can deviate left or right if there is a local density gradient at the focus spot. After propagating beyond the focus, the sound wave diverges and is multiply scattered. Some of this sound undergoes so much multiple scattering that it finally exits the target 134, upon which a fraction is detected by the two receiving detectors 122, 124. Imbalances in the two received signals are dominantly caused by density gradients at the focal plane 130 rather than at other planes where the sound wave is so diffuse that density gradients become averaged out. In some embodiments, the target 134 can be, for example, a subject or patient (e.g. organ tissue) or a physical object (e.g., a wall or pipe) having a target feature 138.

In accordance with some embodiments of the invention, the transmitting transducer 110 can send continuous sound waves (narrowband) into the target 134. In this embodiment, the system 100 can use lock-in detection to isolate the difference signal at the carrier frequency. In accordance with some embodiments of the invention, the transmitting transducer 110 can send sound pulses (broadband) in the target 134. In this embodiment, it may be preferable to rectify the difference signal, and then integrate.

To obtain en-face 2D maps of density gradients, some embodiments of the invention can be configured to scan over the surface (e.g., of a subject, patient or a physical object) for example, using a robot, stage or gantry. In accordance with some embodiments of the invention, a 2D phased-array transducer can be used to provide very fast x-y scanning of a surface. In accordance with some embodiments of the invention, a 1D phased-array transducer can be used to provide fast scanning in the one direction (e.g., the x direction), and be combined with slower mechanical scanning (e.g., using a robot, stage or gantry) in another direction (e.g. the y direction) to selectively (or completely) cover a surface or a portion of a surface. In accordance with some embodiments, mechanical scanning (e.g. using a robot, stage or gantry) can be performed in both x and y directions to selectively (or completely) cover a surface or a portion of a surface.

In accordance with some embodiments of the invention, the target can be a subject (e.g., animal), a person or a physical object. The target can be an US phantom purchased from a commercial source and incorporate calibrated inclusions designed to mimic human tissue (e.g. ATS Laboratories, Gammex, CIRS Inc., etc.).

US imaging by mechanical 2D scanning of a single-element focusing transducer is known as scanning acoustic microscopy [27], [28]. However, this technique is based on the detection of directly reflected sound from the focal plane rather than of transmitted sound that has been subsequently backscattered, as proposed here. As such, a scanning OBUS system according to the invention will produce qualitatively very different images. Another advantage of the OBUS system according to some embodiments of the invention is that it can provide both phase-gradient and amplitude contrasts simultaneously. In accordance with some embodiments of the invention, the system 100 can produce amplitude contrast images by summing the two receive signals.

Generally, the acoustic energy loss in tissue is approximately 0.5 dB/cm/MHz [1]. For example, if the total pathlength of the sound wave from transmitter to receiver is, for example, 10-100 cm (taking multiple scattering into account), then the acoustic loss can be anywhere from a factor of 3 to 100,000. Generally, signal levels in standard US imaging are typically on the order of a few percent relative to transmit levels [2], using very small receiver transducer sizes. In accordance with some embodiment, system 100 can include relatively large receiver transducer sizes (e.g. several millimeters), which should enable the system 100 to easily detect at the fraction of a percent level. In accordance with some embodiments, RF-amplifiers (e.g. MiniCircuits) can be added to the detection system.

In accordance with some embodiments, it can be desirable to operate at low frequencies and low power levels to avoid to burning the target (e.g., tissue). Some embodiments of the system 100 can operate at relatively low frequencies (e.g., 0.1-20 MHz) with non-HIFU (e.g., high intensity focused ultrasound) transducers. In accordance with some embodiments, high powers can be used with lower acoustic frequencies and transducers that produce weaker foci (thus sacrificing spatial resolution).

Figure 6B:
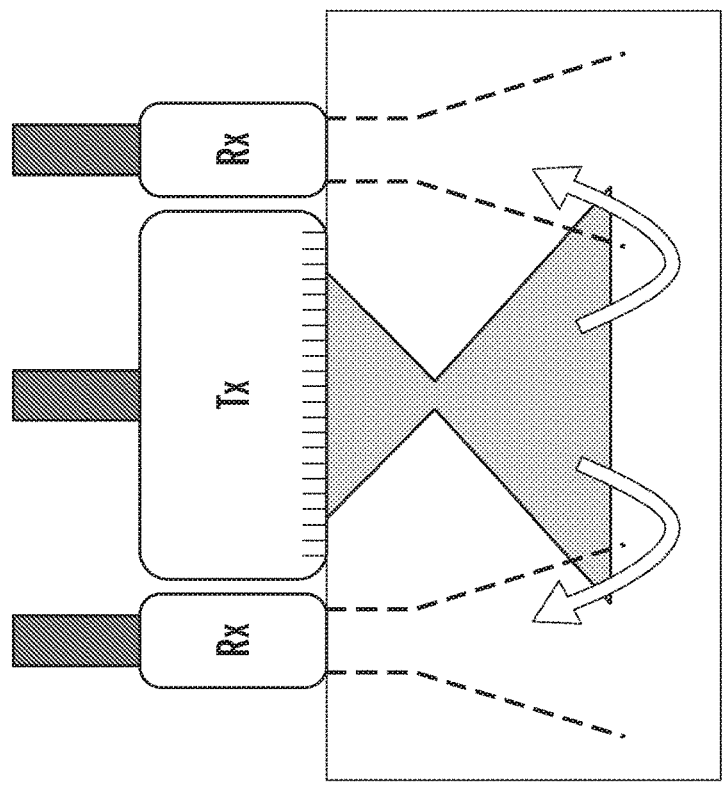
FIGS. 6A and 6B show schematic diagrams of OBUS imaging geometries according to the invention.
Figure 6A:
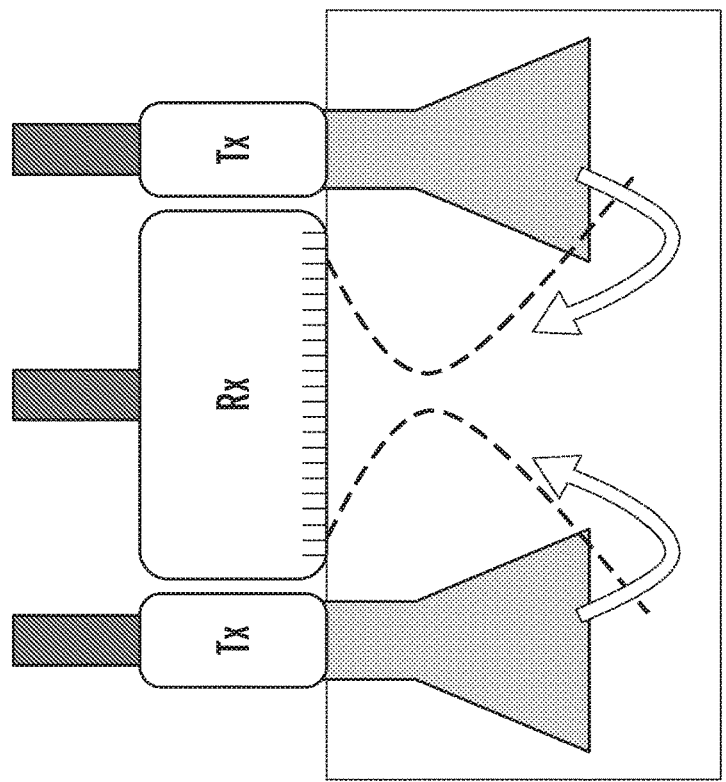

FIGS. 6A and 6B show different OBUS systems configurations according to various embodiments of the invention. For example, FIG. 6A shows a transceiver unit that includes two single-element transducers (Tx) that transmit acoustic signals (e.g., ultrasound) into the target, and an array of receiving/sensing transducers (Rx) that detect diffusively backscattered acoustic signals through a virtual focus produced by phased-array detection. Transmission (Tx) can occur sequentially or at different acoustic frequencies. In this embodiment, virtual or electronic scanning can be achieved along the Rx axis, and orthogonal scanning can be achieved by mechanical scanning (e.g., using a robot, stage or gantry) of the transceiver unit (out of page). This configuration is similar to the optical analog, OBM discussed herein. Alternatively, FIG. 6B shows a transceiver unit wherein the focused acoustic signals (e.g. ultrasound) can be delivered into the target by a phase-array transmitter (Tx) and diffusively back-scattered acoustic signals (e.g., ultrasound) can be detected by the flanking receivers (Rx) on either side of the transmitter (Tx). In this embodiment, virtual or electronic scanning can be achieved along the Tx axis, and orthogonal scanning can be achieved by mechanical scanning (e.g., using a robot, stage or gantry) of transceiver unit (out of page). This configuration is similar to the optical analog, sOBM discussed herein.

Figure 7:
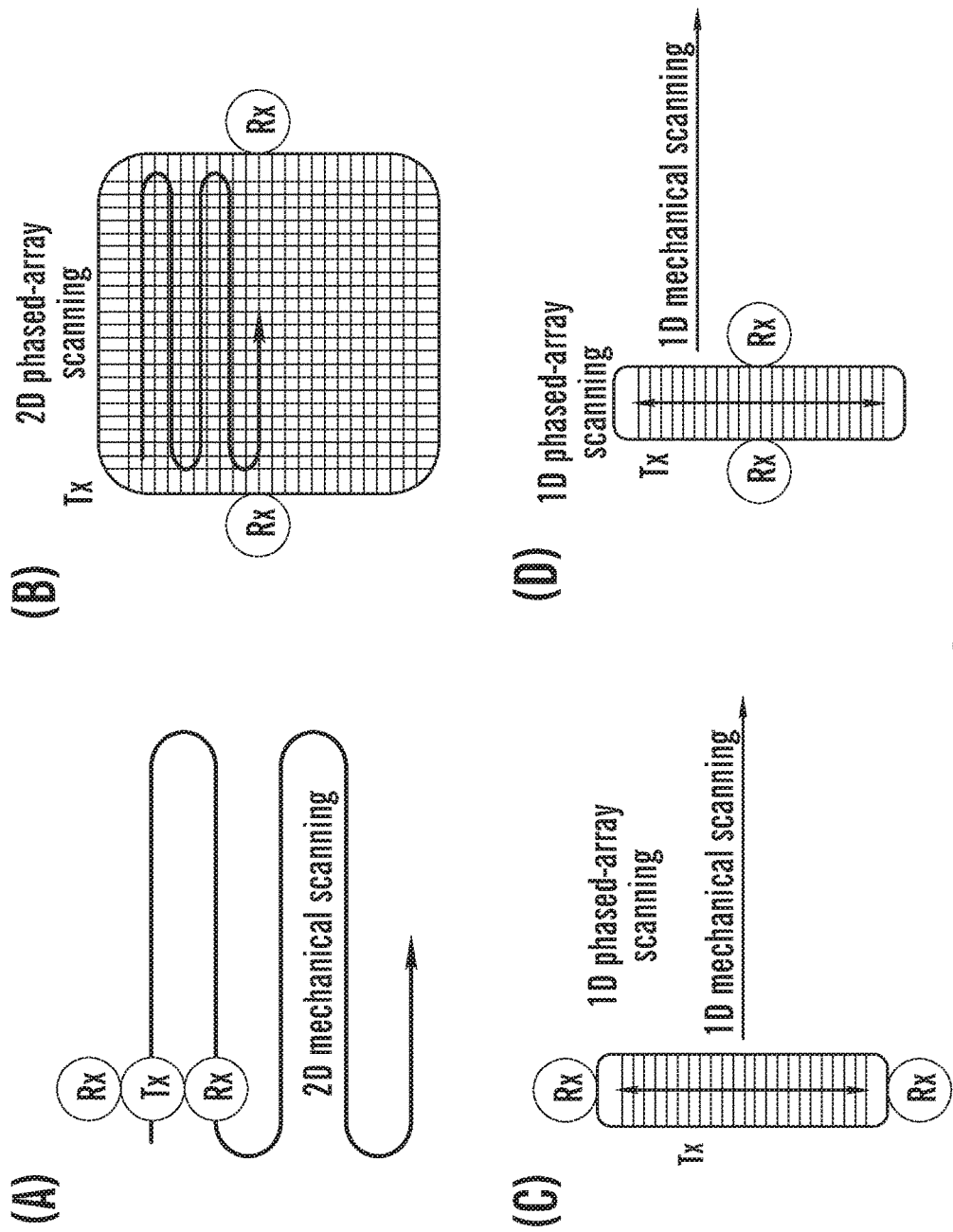
FIG. 7 shows different 2D scanning geometries shown from above: (A) shows a single-element focusing transmitter Tx, and two or more flanking single-element receivers Rx. The entire transceiver unit can be mechanically scanned in 2D. (B) shows a 2D phased-array transmitter Tx that can focus sound and produce C scans, and two or more flanking single-element receivers Rx. 2D scanning in this case is purely electronic. (C) shows a 1D phased-array transducer Tx that can focus sound and produce a 1D B scan, and two or more flanking single element receivers Rx. 2D scanning in this case is partly electronic and partly mechanical. (D) shows a configuration similar to (C) but with different layout of receivers.

FIG. 7 shows different 2D scanning geometries as viewed from above. View (A) shows a single-element focusing transmitter Tx, and two flanking single-element receivers Rx. The entire transceiver unit can be mechanically scanned in 2D. View (B) shows a 2D phased-array transmitter Tx that can focus sound and produce C scans, and flanking single-element receivers Rx. 2D scanning in this embodiment can be accomplished virtually (e.g., electronically). View (C) shows a 1D phased-array transducer Tx that can focus sound and produce a 1D B scan, and two flanking single element receivers Rx. 2D scanning in this embodiment can be accomplished partly electronic and partly mechanically. View (D) shows that same as view (C) but with a different layout of the two receivers (Rx).

Figure 8:
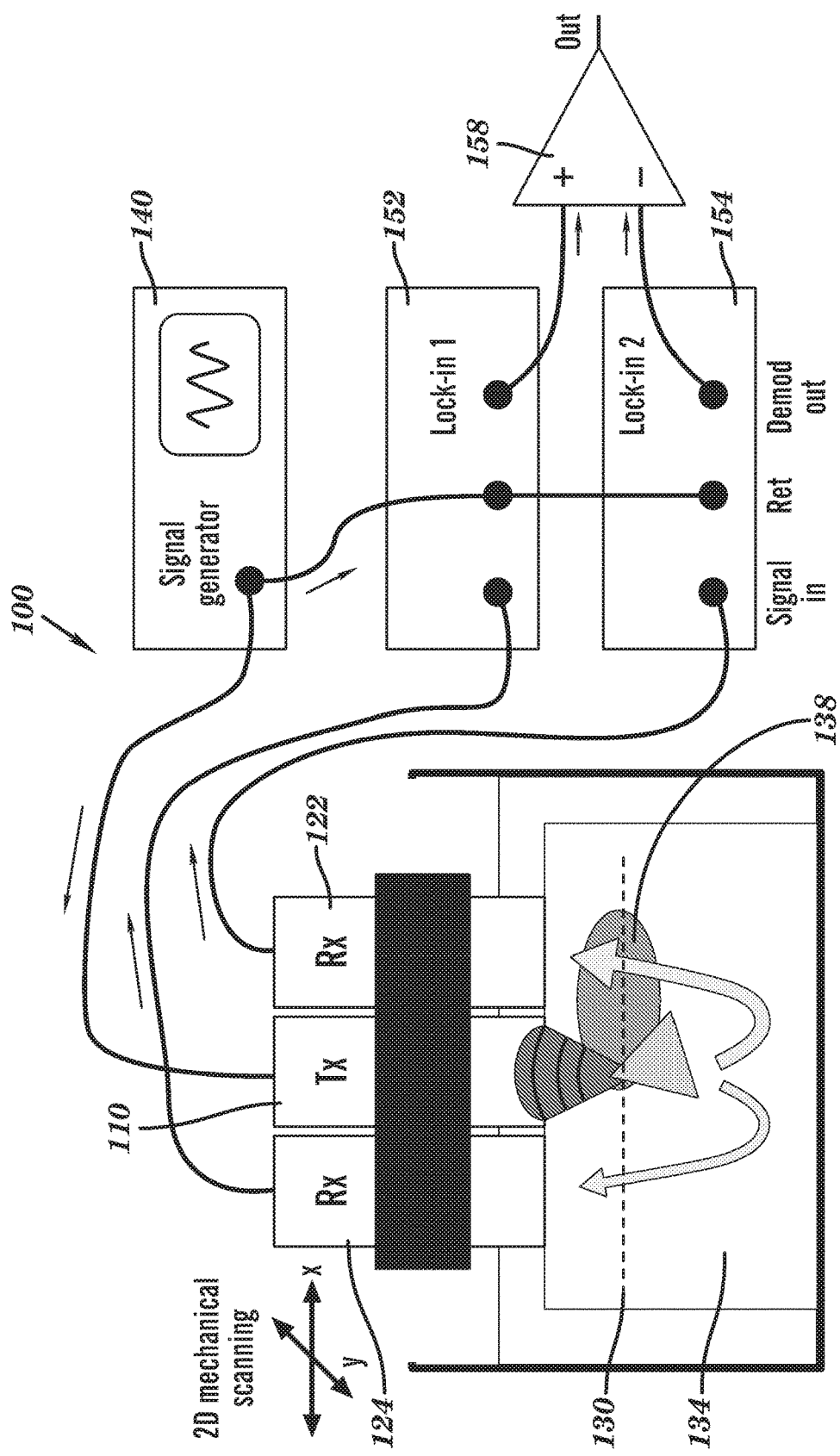
FIG. 8 shows a more detailed version of FIG. 5 according to the invention. A single-element focusing transmitter (Tx) sends sound into the target, and two flanking receivers (Rx) detect diffusively backscattered sound that has interacted with a target feature (e.g. inclusion shown in brown). In this example, continuous sound is produced by a signal generator. Synchronous detection is achieved by dual lock-in detectors. The demodulated-out signals can be of phase or amplitude. A difference of these signals produces phase-gradient contrast; a sum of these signals (not shown) produces absorption contrast. Mechanical 2D scanning of transceiver unit can be the same as shown in FIG. 6B

FIG. 8 shows a more detailed version of the system 100 shown in FIG. 5. The transceiver unit can include a single-element focusing transmitter (Tx) 110 can send acoustic signals (e.g., ultrasound) into the target 134, and two flanking receivers (Rx) 122, 124 detect diffusively backscattered acoustic signals that have interacted with a target feature 138 (e.g. inclusion shown in a darker shade). In this embodiment, continuous acoustic signals can be produced by a signal generator 140, such as a conventional US signal generator. Synchronous detection can be achieved by dual lock-in detectors 152, 154, such as part of conventional US signal processing systems. The demodulated-out signals can be of phase or amplitude. A component 158 of the signal processing system can be used to produce the difference and/or sum of the signals from the two detectors. A difference of these signals can be used by the signal processing system to produce phase-gradient contrast signals and images and a sum of these signals can be used by the signal processing system to produce absorption contrast signals and images. The signals can be processed according to conventional US signal processing systems to generate US images. The signals received by the receivers can be processed by a detection signal processing system that can include conventional US front end and back end processing systems that control the transmit and receive transducers for the various modes of operation and process the raw received signals and convert them into images. Mechanical 2D scanning of the transceiver unit (110, 122, 124) can be the same as shown in FIGS. 6A and 7. In accordance with some embodiments of the invention, each of the transducers 110, 122, 124 can be configurable dual function, transmitting and receiving transducers that can be controlled by a control system to selectively operate in either transmit mode or receive mode.

Figure 9:
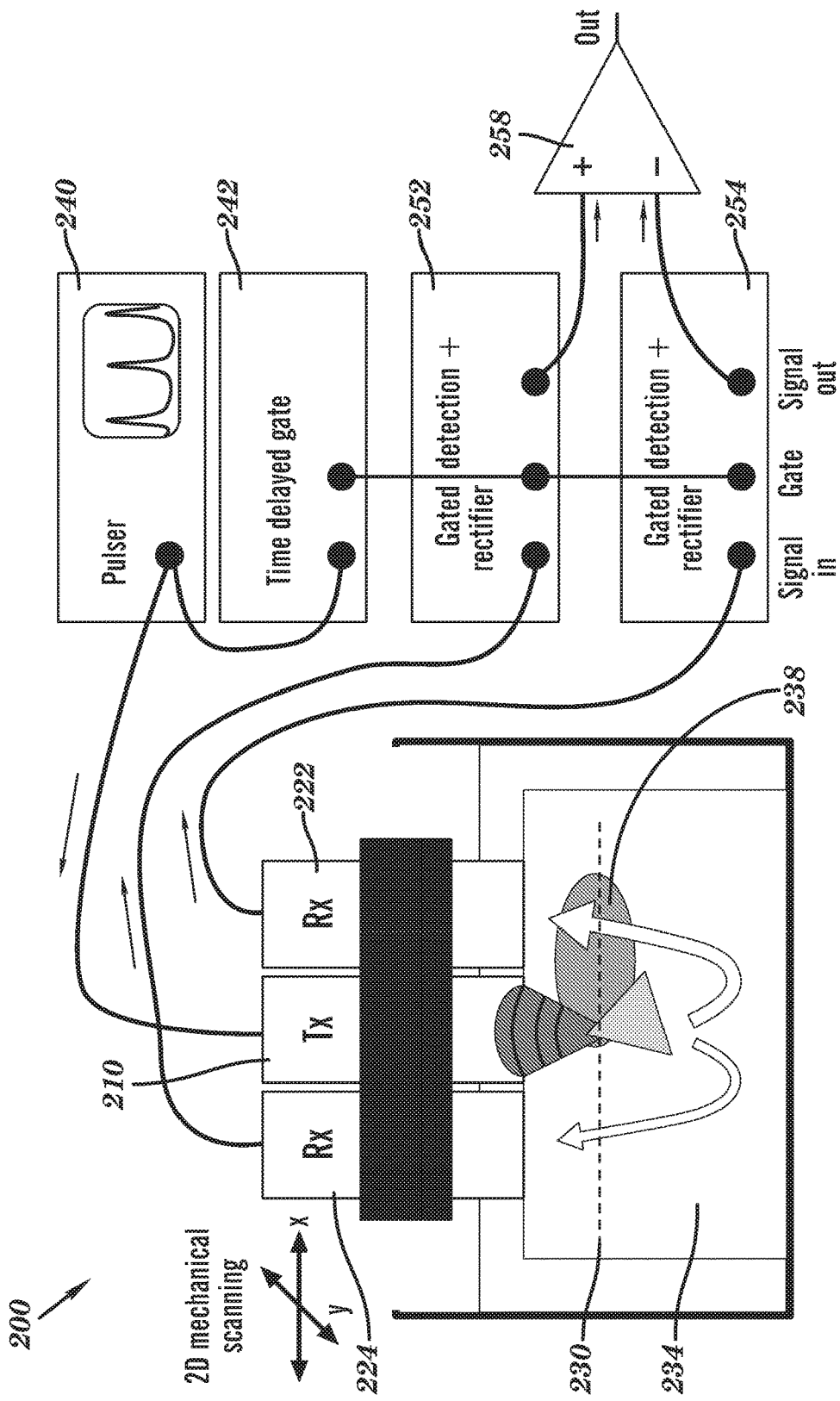
FIG. 9 shows an embodiment of the OBUS system configured to use pulsed acoustic signals according to the invention.

FIG. 9 shows an alternative embodiment of the OBUS system 200 accord to the invention. This embodiment can be configured to use pulsed rather than continuous acoustic signals. A pulser can send acoustic pulses to the transmitter. The receivers can be gated to receive signals with a slight time delay relative to the transmit pulses, where the time delay can be selectively chosen to be long enough to reject direct back-reflections from the surface interface or from objects at depths down to the focal plane. Such gating ensures that only diffuse backscattering is detected. The detected signals can be rectified or squared, filtered, and subtracted or added to yield phase gradient or amplitude contrast respectively.

The system 200 shown in FIG. 9 includes a transceiver unit that can include a single-element focusing transmitter (Tx) 210 that can send acoustic signals (e.g., ultrasound) into the target 234, and two flanking receivers (Rx) 222, 224 detect diffusively backscattered acoustic signals that have interacted with a target feature 238 (e.g. inclusion shown in a darker shade). The pulser 240 can send acoustic pulse signals to the transmitter (Tx) 210 and a time delayed gate 242 can control the delay and duration of an electronic gate controlling the rectifiers 252, 254. The time delay can be selected or chosen to reject unwanted reflections based on the properties (e.g., density) of the target 234 to capture the diffuse backscattering The signals from the receivers (Rx) 222, 224 can be selectively gated and rectified by gated detection rectifiers 252, 254, connected to the receivers (Rx) 222, 224, such as part of a signal processing system. A component 258 of the signal processing system can be used to produce the difference and/or sum of the gated, rectified outputs from the two detectors. A difference of these signals can be used by the signal processing system to produce phase-gradient contrast signals and images and a sum of these signals can be used by the signal processing system to produce absorption contrast signals and images. The signals can be processed according to conventional US signal processing systems to generate US images. The signals received by the receivers can be processed by a detection signal processing system that can include conventional US front end and back end processing systems that control the transmit and receive transducers for the various modes of operation and process the raw received signals and convert them into images. Mechanical 2D scanning of the transceiver unit (210, 222, 224) can be the same as shown in FIGS. 6A, 7 and 8. In accordance with some embodiments of the invention, each of the transducers 210, 222, 224 can be configurable dual function, transmitting and receiving transducers that can be controlled by a control system to selectively operate in either transmit mode or receive mode.

REFERENCES

Each of the references identified below is hereby incorporated by reference in its entirety.

[1] R. S. C. Cobbold, Foundations of Biomedical Ultrasound. Oxford University Press, 2007.
[2] T. L. Szabo, Diagnostic Ultrasound Imaging: Inside Out, 2nd ed. Acad. Press, 2013.
[3] T. N. Ford, K. K. Chu, and J. Mertz, "Phase-gradient microscopy in thick tissue with oblique back-illumination," Nat. Methods, vol. 9, no. 12, pp. 1195-7, December 2012.
[4] T. N. Ford and J. Mertz, "Video-rate imaging of microcirculation with single-exposure oblique back-illumination microscopy single-exposure oblique back-illumination microscopy."
[5] J. D. Giese, T. N. Ford, and J. Mertz, "Fast volumetric phase-gradient imaging in thick samples," vol. 22, no. 1, pp. 21843-21848, 2014.
[6] J. Mertz, Introduction to Optical Microscopy. Roberts & Co., 2009.
[7] F. Zernike, "How I discovered phase contrast," Science (80-.), vol. 121, pp. 345-349, 1955.
[8] G. Nomarski, "Microinterferometer differentuiel a ondes polarisees," J. Phys. Radium., vol. 16, p. S9, 1955.
[9] R. D. Allen, G. B. David, and G. Nomarski, "The Zeiss-Nomarski differential interference equipment for transmitted light microscopy," Z. Wiss. Mikrosk., vol. 69, pp. 193-221, 1969.
[10] J. G. Dodd, "Interferometry with Schlieren microscopy," Appl. Opt., vol. 16, pp. 470-472, 1977.
[11] R. Hoffman and L. Gross, "Modulation contrast microscopy," Appl. Opt., vol. 14, pp. 1169-1176, 1975.
[12] H. U. Dodt, M. Eder, A. Frick, and W. Zieglg\"ansberger, "Precisely localized LTD in the neocortex revealed by infrared-guided laser stimulation," Science (80-.), vol. 286, no. 5437, p. 110, 1999.
[13] R. Yi, K. K. Chu, and J. Mertz, "Graded-field microscopy with white light," Opt. Express, vol. 14, pp. 5191-5200, 2006.
[14] K. K. Chu, R. Yi, and J. Mertz, "Graded-field autoconfocal microscopy," Opt. Express, vol. 15, no. 5, pp. 2476-2489, 2007.
[15] S. B. Mehta and C. J. R. Sheppard, "Quantitative phase-gradient imaging at high resolution with asymmetric illumination-based differential phase contrast.," Opt. Lett., vol. 34, no. 13, pp. 1924-6, July 2009.
[16] R. Yi, K. K. Chu, and J. Mertz, "Graded-field microscopy with white light," Opt. Express, vol. 14, no. 12, pp. 5191-5200, 2006.
[17] J. Fujimoto, "Optical coherence tomography for ultrahigh resolution in vivo imaging," Nat. Biotechnol., vol. 21, no. 11, pp. 1361-1367, 2003.
[18] J. Mertz, a Gasecka, a Daradich, I. Davison, and D. Cote, "Phase-gradient contrast in thick tissue with a scanning microscope.," Biomed. Opt. Express, vol. 5, no. 2, pp. 407-16, February 2014.
[19] W. Welford, "On the relationship between the modes of image formation in scanning microscopy and conventional microscopy," J. Microsc., vol. 96, pp. 104-107, 1972.
[20] M. E. Barnett, "The reciprocity theorem and the equivalence of conventional and transmission microscopes," Optik (Stuttg), vol. 38, pp. 585-588, 1973.
[21] D. Kermisch, "Principle of equivalence between scanning and conventional optical imaging systems," J. Opt. Soc. Am, vol. 67, no. 1357-1360, 1977.
[22] C. J. R. Sheppard and T. Wilson, "On the equivalence of scanning and conventional microscopes," Optik (Stuttg), vol. 73, pp. 39-43, 1986.
[23] H. von Helmholtz, Handbuch der Physiologischen Optik. Leipzig: Leopold Voss, 1856.
[24] Lord Rayleigh, "Some general theorems relating to vibrations," Proc. Lond. Math. Soc., vol. 4, no. 357-368, 1873.
[25] M. M. Burlew, M. E. L., and J. A. Zagzebsky, "A new ultrasound tissue-equivalent material," Radiology, vol. 134, p. 517, 1980.
[26] R. O. Bude and R. S. Adler, "An Easily Made, Low-Cost, Tissue-Like Ultrasound Phantom Material," J. Clin. Ultrasound, vol. 23, pp. 271-273, 1995.
[27] R. N. Johnston, a Atalar, J. Heiserman, V. Jipson, and C. F. Quate, "Acoustic microscopy: resolution of subcellular detail," Proc. Natl. Acad. Sci. U.S.A., vol. 76, no. 7, pp. 3325-9, July 1979.
[28] J. a Hildebrand, D. Rugar, R. N. Johnston, and C. F. Quate, "Acoustic microscopy of living cells," Proc. Natl. Acad. Sci. U.S.A., vol. 78, no. 3, pp. 1656-60, March 1981.
[29] A. Dubois, L. Vabre, A. C. Boccara, and E. Beaurepaire, "High-resolution full-field optical coherence tomography with a Linnik microscope," Appl. Opt., vol. 41, pp. 805-812, 2002.

Other embodiments are within the scope and spirit of the invention. For example, due to the nature of software, the US signal processing functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. An oblique backscatter acoustic imaging system comprising:
    a transmitting transducer configured to produce focused acoustic waves propagating into and through a target;
    two or more receiving transducers positioned on opposite sides of the transmitting transducer and configured to detect diffuse backscatter of the acoustic waves passing through the target; and
    a signal processor configured to receive a signal from at least one of the receiving transducers representative of the detected backscatter of the acoustic waves that have passed through the target and produce a signal representative of at least one of a phase-gradient contrast signal or an absorption contrast signal from the received signal.

2. The oblique backscatter acoustic imaging system according to claim 1 wherein the transmitting transducer includes a one dimensional array of acoustic transmitting transducers.

3. The oblique backscatter acoustic imaging system according to claim 1 further comprising a scanning mechanism for moving the transmitting transducer and the two or more receiving transducers across an area of the target.

4. The oblique backscatter acoustic imaging system according to claim 1 wherein the transmitting transducer includes a two dimensional array of acoustic transmitting transducers.

5. The oblique backscatter acoustic imaging system according to claim 1 wherein the transmitting transducer is connected to an acoustic signal generator and the signal processor includes at least one detector configured to produce a demodulated signal representative of the backscatter acoustic waves received by at least one of the receiving transducers.

6. The oblique backscatter acoustic imaging system according to claim 5 wherein the signal processor includes at least two lock-in detectors, one connected to each receiving transducer and a signal processing component connected to the at least two lock-in detector and configured to receive demodulated signals from each receiving transducer and produce a signal representative of a difference between the received demodulated signals.

7. The oblique backscatter acoustic imaging system according to claim 5 wherein the signal processor includes at least two lock-in detectors, one connected to each receiving transducer and a signal processing component connected to the at least two lock-in detector and configured to receive demodulated signals from each receiving transducer and produce a signal representative of a sum of the received demodulated signals.

8. The oblique backscatter acoustic imaging system according to claim 1 wherein the transmitting transducer is connected to a pulsing acoustic signal generator and the signal processor includes at least one gated detection rectifier configured to produce an output signal representative of the backscatter acoustic waves received at least one of the receiving transducers.

9. The oblique backscatter acoustic imaging system according to claim 8 wherein the signal processor includes a time delayed gate and at least two gated detection rectifiers, one connected to each receiving transducer and a signal processing component connected to the at least two gated detection rectifiers and configured to receive output signals from each receiving transducer and produce a signal representative of a difference between the received output signals.

10. The oblique backscatter acoustic imaging system according to claim 8 wherein the signal processor includes a time delayed gate and at least two gated detection rectifiers, one connected to each receiving transducer and a signal processing component connected to the at least two gated detection rectifiers and configured to receive output signals from each receiving transducer and produce a signal representative of a sum of the received output signals.

11. An oblique backscatter acoustic imaging system comprising:
    two or more transmitting transducers, each configured to produce acoustic waves propagating into and through a target;
    a receiving transducer positioned between the transmitting transducers and adapted to detect diffuse backscatter of the acoustic waves passing through the target; and
    a detector signal processor adapted to receive a signal from the receiving transducer representative of the detected backscatter of the acoustic waves that have passed through the target and produce a signal representative of at least one of a phase-gradient contrast signal or an absorption contrast signal from the received signal.

12. The oblique backscatter acoustic imaging system according to claim 11 wherein the receiving transducer includes a one dimensional array of acoustic receiving transducers.

13. The oblique backscatter acoustic imaging system according to claim 11 further comprising a scanning mechanism for moving the two or more transmitting transducers and the receiving transducer across an area of the target.

14. The oblique backscatter acoustic imaging system according to claim 11 wherein the receiving transducer includes a two dimensional array of acoustic receiving transducers.

* * * * *